United States Patent [19]

Pettersson

[11] Patent Number: 5,444,167

[45] Date of Patent: Aug. 22, 1995

[54] VARIANT LUTEINIZING HORMONE ENCODING DNA

[75] Inventor: Kim S. I. Pettersson, Turku, Finland

[73] Assignee: Wallac Oy, Turku, Finland

[21] Appl. No.: 86,915

[22] Filed: Jul. 7, 1993

[51] Int. Cl.⁶ .............................................. C07H 21/04
[52] U.S. Cl. .................. 536/23.51; 536/23.5
[58] Field of Search ................... 536/23.5, 23.51, 23.5, 536/23.51, 23.5

[56] References Cited

PUBLICATIONS

Lehninger, A. L. Biochemistry, Second Edition, May 1976, p. 962.
Maurer, R. A. Analysis of Several Bovine Lutropinβ Subunit cDNAs Reveals Heterogeneity in Nucleotide Sequence, J. Biol. Chem (Apr. 25, 1985) 260:4684–4687.

*Primary Examiner*—Margaret Parr
*Assistant Examiner*—David Schreiber
*Attorney, Agent, or Firm*—Ronald J. Kubovcik

[57] ABSTRACT

The invention relates to a DNA molecule with the sequence coding for a mammalian luteinizing hormone wherein the codon for the amino acid located at position 8 of the LHβ chain is replaced by a codon for arginine or the codon for isoleucine at position 15 of the LHβ chain is replaced by a codon for threonine.

7 Claims, 3 Drawing Sheets

```
SEQ ID NO:              -1    1                                      8
    1    GGC GGG GCA TGG GCA TCC AGG GAG CCG CTT CGG CCA TGG TGC  (lit.)
    2    ----------------------------------------------C-------- V-LH 10              15                20
         CAC CCC ATC AAT GCC ATC CTG GCT GTG GAG AAG GAG GGC TGC
         ---------------------C----------------------------------

25              30                35
         CCC GTG TGC ATC ACC GTC AAC ACC ACC ATC TGT GCC GGC TAC
         --------------------------------------------------------

40
         TGC CCC ACC ATG
         --------------
```

| SEQ ID NO: | | SEQ ID NO: | |
|---|---|---|---|
| 3 | LH I Forward 17 mer; $T_m$=56.6°C<br>5' GGG GCA TGG GCA TCC AG 3' | 4 | LH I Reverse 18 mer; $T_m$=58.2°C<br>5' CCATTCCCCAACCGCAGG 3' |
| 5 | LH II Forward 18mer; $T_m$=57.4°C<br>5' GCCTCTCTGGCCTGCGGT 3' | 6 | LH II Reverse 16 mer; $T_m$=58.7°C<br>5' GCCCTG CAG CAC GCG CA 3' |
| 7 | LH III Forward 21mer; $T_m$=57.7°C<br>5' CAC TCA CAC GGC CTCCAG ATG 3' | 8 | LH III Reverse 21 mer; $T_m$=56.6°C<br>5' G ACA GCT GAG AGC CAC AGG GA 3' |
| 9 | LH IV Forward 19mer; $T_m$=57.4°C<br>5' C CCC GTG GTCTCCTTCCCT 3' | 10 | LH IV Reverse 18 mer; $T_m$=58.8°C<br>5' CGGGGGTGTCAGGGCTCCA 3' |

FIG.1

SEQ ID NO:
1    GGC GGG GCA TGG GCA TCC AGG GAG CCG CTT CGG CCA TGG TGC (lit.)
2    ------------------------------------------------C-------  V-LH 10                              15                           20
     CAC CCC ATC AAT GCC ATC CTG GCT GTG GAG AAG GAG GGC TGC
     ------------------------C-------

25                              30                           35
     CCC GTG TGC ATC ACC GTC AAC ACC ACC ATC TGT GCC GGC TAC

40
     TGC CCC ACC ATG

FIG.2

```
SEQ ID NO:                950                      -1
   11                     GLY-GLY-ALA-TRP-ALA-          1.
   12                     ------------------           2.
   13                     ------------------           3.
   14                     --------THR-------           4.

+1          +5                    +10
        SER-ARG-GLU-PRO-LEU-ARG-PRO-TRP-CYS-HIS-       1. hLH (lit.)
        --------------------------ARG-------           2. V-LH, TL
        ----------------------------------             3. N-LH, KP
        ----LYS-------------------ARG-----ARG-         4. hCG (lit.)
   15   --------GLY-------------------LEU-----GLN-     5. o,b LH (lit.)
   16   --------GLY-------------------LEU-----ARG-     6. r LH (lit.)
   17   --------GLY-------------------LEU-----ARG-     7. p LH (lit.)

+15                   +20
        PRO-ILE-ASN-ALA-ILE-LEU-ALA-VAL-GLU-LYS-       1.
        --------------THR-------------------           2.
        ------------------------------------           3.
        ----------*-----THR-----------------           4.

----------*-----THR---------ALA-----           5.
        ----------------THR---------ALA-----ASN-       6.
        ----------*-----THR-----------------           7.

+25                   +30
                                           *
        GLU-GLY-CYS-PRO-VAL-CYS-ILE-THR-VAL-ASN-       1.
        --------------------------------------         2.
        --------------------------------------         3.
        -----------------------------------*--         4.

---ALA--------------------------PHE-THR-       5.
        ---PHE--------------------------PHE-THR-       6.
        ---ALA--------------------------PHE-THR-       7.

+35                   +40
        THR-THR-ILE-CYS-ALA-GLY-TYR-CYS-PRO-THR-MET    1.
        ------------------------------------------    2.
        ------------------------------------------    3.
        ------------------------------------------    4.

---SER-------------------------SER--------    5.
        ---SER-------------------------SER--------    6.
        ---SER------------------------------------    7.
```

FIG.3

SEQUENCE LISTING ( 1 ) GENERAL INFORMATION:

( i i i ) NUMBER OF SEQUENCES: 17

( 2 ) INFORMATION FOR SEQ ID NO:1:

```
( i ) SEQUENCE CHARACTERISTICS:
        ( A ) LENGTH: 138 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:1:
```

GGCGGGGCAT GGGCATCCAG GGAGCCGCTT CGGCCATGGT GCCACCCCAT CAATGCCATC    60

CTGGCTGTGG AGAAGGAGGG CTGCCCCGTG TGCATCACCG TCAACACCAC CATCTGTGCC    120

GGCTACTGCC CCACCATG                                                  138

( 2 ) INFORMATION FOR SEQ ID NO:2:

```
( i ) SEQUENCE CHARACTERISTICS:
        ( A ) LENGTH: 138 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens
        ( D ) DEVELOPMENTAL STAGE: Adult ( x i ) SEQUENCE DESCRIPTION: SEQ ID NO:2:
```

GGCGGGGCAT GGGCATCCAG GGAGCCGCTT CGGCCACGGT GCCACCCCAT CAATGCCACC    60

CTGGCTGTGG AGAAGGAGGG CTGCCCCGTG TGCATCACCG TCAACACCAC CATCTGTGCC    120

GGCTACTGCC CCACCATG                                                  138

( 2 ) INFORMATION FOR SEQ ID NO:3:

```
( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:
```

GGGGCATGGG CATCCAG                                                   17

( 2 ) INFORMATION FOR SEQ ID NO:4:

```
( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:
```

CCATTCCCCA ACCGCAGG                                                  18

( 2 ) INFORMATION FOR SEQ ID NO:5:

```
( i ) SEQUENCE CHARACTERISTICS:
        ( A ) LENGTH: 18 base pairs
```

(B) TYPE: nucleic acid
(C) STRANDEDNESS: single
(D) TOPOLOGY: linear (xi) SEQUENCE DESCRIPTION: SEQ ID NO:5:

GCCTCTCTGG CCTGCGGT                                          18

(2) INFORMATION FOR SEQ ID NO:6:

(i) SEQUENCE CHARACTERISTICS:
(A) LENGTH: 16 base pairs
(B) TYPE: nucleic acid
(C) STRANDEDNESS: single
(D) TOPOLOGY: linear (xi) SEQUENCE DESCRIPTION: SEQ ID NO:6:

GCCTGCAGCA CGCGCA                                            16

(2) INFORMATION FOR SEQ ID NO:7:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:7:

CACTCACACG GCCTCCAGAT G                                      21

(2) INFORMATION FOR SEQ ID NO:8:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:8:

GACAGCTGAG AGCCACAGGG A                                      21

(2) INFORMATION FOR SEQ ID NO:9:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:9:

CCCCGTGGTC TCCTTCCCT                                         19

(2) INFORMATION FOR SEQ ID NO:10:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:10:

CGGGGTGTCA GGGCTCCA                                          18

(2) INFORMATION FOR SEQ ID NO:11:

(i) SEQUENCE CHARACTERISTICS:
(A) LENGTH: 46 amino acids
(B) TYPE: amino acid
(D) TOPOLOGY: linear (ii) MOLECULE TYPE: protein (i i i) HYPOTHETICAL: NO (v i) ORIGINAL SOURCE:
    (A) ORGANISM: Homo sapiens (i x) FEATURE:
    (A) NAME/KEY: Modified-site
    (B) LOCATION: 30
    (D) OTHER INFORMATION: /note="The asparagine at position 30 is linked to an oligosaccharide."

(x i) SEQUENCE DESCRIPTION: SEQ ID NO:11:

```
Gly Gly Ala Trp Ala Ser Arg Glu Pro Leu Arg Pro Trp Cys His Pro
 -5              1               5                  10
Ile Asn Ala Ile Leu Ala Val Glu Lys Glu Gly Cys Pro Val Cys Ile
             15              20              25
Thr Val Asn Thr Thr Ile Cys Ala Gly Tyr Cys Pro Thr Met
         30              35              40
```

(2) INFORMATION FOR SEQ ID NO:12:

(i) SEQUENCE CHARACTERISTICS:
        (A) LENGTH: 46 amino acids
        (B) TYPE: amino acid
        (D) TOPOLOGY: linear (i i) MOLECULE TYPE: protein (v i) ORIGINAL SOURCE:
        (A) ORGANISM: Homo sapiens (x i) SEQUENCE DESCRIPTION: SEQ ID NO:12:

```
Gly Gly Ala Trp Ala Ser Arg Glu Pro Leu Arg Pro Arg Cys His Pro
 -5              1               5                  10
Ile Asn Ala Thr Leu Ala Val Glu Lys Glu Gly Cys Pro Val Cys Ile
             15              20              25
Thr Val Asn Thr Thr Ile Cys Ala Gly Tyr Cys Pro Thr Met
         30              35              40
```

(2) INFORMATION FOR SEQ ID NO:13:

(i) SEQUENCE CHARACTERISTICS:
        (A) LENGTH: 46 amino acids
        (B) TYPE: amino acid
        (D) TOPOLOGY: linear (i i) MOLECULE TYPE: protein (i i i) HYPOTHETICAL: NO (v i) ORIGINAL SOURCE:
        (A) ORGANISM: Homo sapiens (x i) SEQUENCE DESCRIPTION: SEQ ID NO:13:

```
Gly Gly Ala Trp Ala Ser Arg Glu Pro Leu Arg Pro Trp Cys His Pro
 -5              1               5                  10
Ile Asn Ala Ile Leu Ala Val Glu Lys Glu Gly Cys Pro Val Cys Ile
             15              20              25
Thr Val Asn Thr Thr Ile Cys Ala Gly Tyr Cys Pro Thr Met
         30              35              40
```

(2) INFORMATION FOR SEQ ID NO:14:

(i) SEQUENCE CHARACTERISTICS:
        (A) LENGTH: 46 amino acids
        (B) TYPE: amino acid
        (D) TOPOLOGY: linear (i i) MOLECULE TYPE: protein ( i i i ) HYPOTHETICAL: NO ( v i ) ORIGINAL SOURCE:
   ( A ) ORGANISM: Homo sapiens ( i x ) FEATURE:
   ( A ) NAME/KEY: Modified-site
   ( B ) LOCATION: 13
   ( D ) OTHER INFORMATION: /note="The asparagine at position 13 is linked to an oligosaccharide."

( i x ) FEATURE:
   ( A ) NAME/KEY: Modified-site
   ( B ) LOCATION: 30
   ( D ) OTHER INFORMATION: /note="The asparagine at position 30 is linked to an oligosaccharide."

( x i ) SEQUENCE DESCRIPTION: SEQ ID NO:14:

```
Gly Gly Thr Trp Ala Ser Lys Glu Pro Leu Arg Pro Arg Cys Arg Pro
-5              1               5                   10

Ile Asn Ala Thr Leu Ala Val Glu Lys Glu Gly Cys Pro Val Cys Ile
            15                  20                  25

Thr Val Asn Thr Thr Ile Cys Ala Gly Tyr Cys Pro Thr Met
        30              35                  40
```

( 2 ) INFORMATION FOR SEQ ID NO:15:

( i ) SEQUENCE CHARACTERISTICS:
       ( A ) LENGTH: 41 amino acids
       ( B ) TYPE: amino acid
       ( D ) TOPOLOGY: linear ( i i ) MOLECULE TYPE: protein ( i i i ) HYPOTHETICAL: NO ( i x ) FEATURE:
       ( A ) NAME/KEY: Modified-site
       ( B ) LOCATION: 13
       ( D ) OTHER INFORMATION: /note="The asparagine at position 13 is linked to an oligosaccharide."

( x i ) SEQUENCE DESCRIPTION: SEQ ID NO:15:

```
Ser Arg Gly Pro Leu Arg Pro Leu Cys Gln Pro Ile Asn Ala Thr Leu
1               5                   10                  15

Ala Ala Glu Lys Glu Ala Cys Pro Val Cys Ile Thr Phe Thr Thr Ser
            20                  25                  30

Ile Cys Ala Gly Tyr Cys Pro Ser Met
        35                  40
```

( 2 ) INFORMATION FOR SEQ ID NO:16:

( i ) SEQUENCE CHARACTERISTICS:
       ( A ) LENGTH: 41 amino acids
       ( B ) TYPE: amino acid
       ( D ) TOPOLOGY: linear ( i i ) MOLECULE TYPE: protein ( x i ) SEQUENCE DESCRIPTION: SEQ ID NO:16:

```
Ser Arg Gly Pro Leu Arg Pro Leu Cys Arg Pro Ile Asn Ala Thr Leu
1               5                   10                  15

Ala Ala Glu Asn Glu Phe Cys Pro Val Cys Ile Thr Phe Thr Thr Ser
            20                  25                  30

Ile Cys Ala Gly Tyr Cys Pro Ser Met
        35                  40
```

( 2 ) INFORMATION FOR SEQ ID NO:17:

( i ) SEQUENCE CHARACTERISTICS:
    ( A ) LENGTH: 41 amino acids
    ( B ) TYPE: amino acid
    ( D ) TOPOLOGY: linear ( i i ) MOLECULE TYPE: protein ( i i i ) HYPOTHETICAL: NO ( i x ) FEATURE:
    ( A ) NAME/KEY: Modified-site
    ( B ) LOCATION: 13
    ( D ) OTHER INFORMATION: /note="The asparagine at position 13 is linked to an oligosaccharide."

( x i ) SEQUENCE DESCRIPTION: SEQ ID NO:17:

```
Ser Arg Gly Pro Leu Arg Pro Leu Cys Arg Pro Ile Asn Ala Thr Leu
 1               5                   10                  15

Ala Val Glu Lys Glu Ala Cys Pro Val Cys Ile Thr Phe Thr Thr Ser
            20                  25                  30

Ile Cys Ala Gly Tyr Cys Pro Thr Met
            35                  40
```

VARIANT LUTEINIZING HORMONE ENCODING DNA

This invention relates to DNA-molecules encoding variants of mammamilian luteinizing hormones.

BACKGROUND OF THE INVENTION

Human lutropin or human luteinizing hormone (hLH) belongs to the glycoprotein hormone family along with human follicle stimulating hormone (FSH), human thyroid stimulating hormone (TSH) and human chorionic gonadotropin (hCG) (for review see Ryan R. J. et al. 1987, Structure-function relationships of gonadotropins. Rec Prog Horm Res 43:383–429). The glycoprotein hormones consist of two subunits. The amino acid sequence of the alpha subunit is identical or nearly identical for the four human glycoprotein hormones. Despite significant homologies between the different glycoprotein hormones, the beta subunit is responsible for the target organ specificity of the hormone. hLH and hFSH which are produced by cells of the pituitary gland, regulates the steroid hormone production in the human gonads. The beta subunits of hLH and hCG are highly homologous. The major difference is the additional 24 amino acid extension at the carboxyterminal of hCGβ subunit. The biological action of hLH and hCG is mediated through the same receptor.

The carbohydrate part plays a significant role in the biological action of the glycoprotein hormones. Chemical deglycosylation has been used to study the function of Asn linked oligosacharide moieties in glycoprotein hormone action. This procedure does not affect the interaction between the alpha and beta dimers nor the binding of the hormone to its receptor. The deglycosylated hormones, however, have significantly reduced ability to stimulate the cAMP production in target cells despite normal binding to the receptor. The biological effect of the hormone is also indirectly influenced by the carbohydrate part, as differences in the structure of the carbohydrate moieties will effect the circulatory half lives of the hormone (Baenziger J. U. et al. 1992. Circulatory half-life but not interaction with the lutropin/chorionic gonadotropin receptor is modulated by sulfation of bovine lutropin oligosacharides. Proc Natl Acad Sci USA 89:334–338). hLH and hCG, although highly similar in peptide sequence and in vitro biological activity, have quite different in vivo biological half lives. The oligosacharides of hLH when synthesized in the gonadotrophs are largely sulfated through mediation of enzyme systems specific for the gonadotroph cells of the pituitary. Increased sulfation gives hLH a shorter circulatory half-life due to removal by hepatic cell receptors specific for the sulfated forms of LH (Fiete D. et al. 1991. A hepatic reticuloendothelial cell receptor specific for $SO_4$-4GalNAcβ1, 4GlcNAcβ1, 2Man-alpha that mediates rapid clearance of lutropin. Cell 67:1103–1110). The carbohydrates of hCG synthesized in trophoblastic cells are not sulfated and therefore the protein has a longer circulatory half-life. Interspecies differences in glycosylation of the same glycoprotein as well as differences between the different glycoprotein hormones are obviously determined partly by differences in peptide sequence and partly by the glycosylation enzymes of the hormone producing cells (for review see Green E. D. et al. 1986. Differential processing of Asn-linked oligosaccharides on pituitary hormones: implications for biologic function. Mol Cell Biochem 72:81–100).

Due to differences in the carbohydrate part of the molecules, the glycoprotein hormones display a multitude of isoforms as seen in separating systems based on charge (Wide L. 1985. Median charge and charge heterogeneity of human pituitary FSH, LH and TSH. I. Zone electrophoresis in agarose suspension. Acta Endocrinol 109:181–189).

The concentration of hormones in biological fluids can be estimated through in vivoor in vitro biological assay systems. However, determinations with immunoassays provide a more convenient way for estimation of hormone concentrations/activites. Differently designed immunoassays constitute the preferred methods of hormone determinations in routine clinical laboratories. With monoclonal antibodies, sensitive detection technologies and non-competitive assay designs, extremely specific and sensitive assay sytems have been optimized.

In a previous work (Pettersson K. S. I et al. 1991, Individual differences in LH immunoreactivity revealed by monoclonal antibodies. Clin Chem 37:333–340) on optimizing non-competitive (sandwich) immunoassays for hLH employing monoclonal antibodies we found that certain monoclonal antibodies recognizing epitopes present on the intact alpha-beta dimer (but not on the free subunits) of LH displayed restrictive reactivity against hLH in some individuals. Depending on the monoclonal antibodies used, the LH immunoactivity in some individuals were either reduced to various degrees or altogether non-detectable. A pedigree study (Pettersson K et al. An immunologically anomalous LH variant in a healthy woman. J Clin Endocrinol Metab 74:164–171, 1992) of the proband initially found (a 31 year old woman with no detectable hLH when employing a certain monoclonal antibody) strongly indicated that these observations were due to a genetic variant of hLH (variant LH [V-LH]) as opposed to normal LH [N-LH]. Measurement of in vitro LH biological activity also showed that hLH of these individuals with immunologically "silent" LH employing certain monoclonal antibodies does possess normal biological activity (Pettersson K et al. An immunologically anomalous LH variant in a healthy woman. J Clin Endocrinol Metab 74:164-171, 1992; Pettersson K et al. 1991, Monoclonal antibody-based discrepancies between two-site immunometric tests for lutropin. Clin Chem 37:1745-1748). Our studies also indicate that the putative heterozygous condition (individuals with both N-LH and VLH) is quite frequent—about 20–25 percent in Finnish and Scandinavian populations (Pettersson K. S. I et al. 1991. Individual differences in LH immunoreactivity revealed by monoclonal antibodies. Clin Chem 37:333–340).

SUMMARY OF THE INVENTION

It has now been discovered that the anomalous form of LH, as displayed through the lack of or reduced interaction with some monoclonal antibodies in our previous studies, is a genetic variant.

The invention thus concerns a DNA molecule with the sequence coding for a mammalian luteinizing hormone characterized in that the codon for the amino acid located at position 8 of the LHβ chain is replaced by a codon for arginine or the codon for isoleucine at position 15 of the LHβ chain is replaced by a codon for threonine.

According to one aspect of the invention, only the codon for the amino acid located at position 8 of the LHβ chain is replaced by a codon for arginine.

According to another aspect of the invention, both the codon for tryptophan located at position 8 of the LHβ chain is replaced by a codon for arginine and the codon for isoleucine at position 15 of the LHβ chain is replaced by a codon for threonine.

The invention concerns DNA molecules encoding variants of human as well as bovine, ovine and porcine luteinizing hormone.

According to a further aspect of the invention, the DNA molecule with the sequence coding for human luteinizing hormone wherein both the codon for tryptophan located at position 8 of the LHβ chain is replaced by a codon for arginine and the codon for isoleucine at position 15 of the LHβ chain is replaced by a codon for threonine, has the codon CGG at position 8 and ACC at position 15.

BRIEF DESCRIPTION OF THE DRAWINGS

FIG. 1 describes the primers used for the PCR and sequencing.

FIG. 2 describes the DNA sequence of the −5 to 41 fragment of hLHβ subunit according to the literature (Ryan R. J. et al.1987, Structure-function relationships of gonadotropins. Rec Prog Horm Res 43:383–429) and according to our sequencing studies of the immunologically variant LH (VLH).

FIG. 3 describes the amino acid partial sequences of variant hLH (V-LH, No.2) and normal hLH (N-LH, No.3) in comparison with published LH and hCG sequence segments according to the literature (Ryan R. J. et al. 1987, Structure-function relationships of gonadotropins. Rec Prog Horm Res 43:383–429). oLH and bLH represent ovine LH and bovine LH, respectively; rLH is rat LH and pLH is porcine LH. In FIG. 3 * indicates Asn or Thr linked oligosaccaride according to Ryan R. J. et al.

DETAILED DESCRIPTION OF THE INVENTION

DNA was isolated from white blood cells of V-LH and N-LH individuals using a standard protocol (Proteinase K, phenol extraction and precipitation with ammonium acetate). The polymerase chain reaction (PCR) technique was utilized to multiply four DNA fragments covering the LHβ gene. Primers for PCR were designed for regions of DNA showing the highest variation between the β genes of hCG and hLH. Four pair of primers (FIG. 1) were designed each having a 3-mismatch for hCGβ and varying from 16 to 21 nucleotides in length. The primers were synthesized using a DNA synthesizer (GeneAssembler Plus).

Taq DNA Polymerase was used in the PCR. 100 ng of DNA was subjected to PCR together with 0.125 μmol/L of the forward and reverse primers, 0.2 mmol/L nucleotides and 5 mmol/L $MgCl_2$. After 35 cycles of PCR, the products were analysed by gel electrophoresis. Restriction enzyme digestions were also used to ensure the quality of the product. In order to obtain enough material for the sequencing, DNA from five PCR reactions were combined. This also served to minimize the influence of possible Taq polymerase induced misreadings in the single PCR runs.

For Sanger's dideoxy method using SEQUENASE TM enzyme was employed. Several sequencing reactions using DNA template from different PCR reactions were performed to obtain the final sequence.

Two point mutations in the DNA from the V-LH individual (TL) were detected (FIG. 2). FIG. 3 shows the hLHβ 1-41 aminoterminal sequence a) according to the published sequence, b) in TL (V-LH individual) and in c) KP, a N-LH control individual. The published sequences for ovine, bovine and porcine LH as well as that of hCG are shown. The aminoacid sequence as determined by the nucleotide sequence obtained in the N-LH individual (KP) was identical to that previously published.

In V-LH, the amino acid at position 8, tryptophan (Trp), is replaced by arginine (Arg), and the amino acid at position 15, isoleucine (Ile) is replaced by threonin (Thr). The amino acid substitutions of the variant hLH are identical to the amino acids in the homologous positions of hCG. Two additional amino acid positions (at 2 and 10) where published sequences of hLH and hCG differs provide additional controls that the correct DNA has been sequenced.

Production of any mammalian LH and preferentially human LH, by recombinant technique may take advantage of these mutated positions of human LH, resulting in a hLH variant retaining normal biological activity.

According to the literature and through comparisons with LH from other species the mutated LH contains the consensus sequence $Asn_{13}$-$Ala_{14}$-$Thr_{15}$ that introduces a new glycosylation site at aminoacid position 13 (as in hCGβ, ovine LHβ, bovine LHβ, and porcine LHβ). Furthermore, the tripeptide sequence $Pro_4$-$Leu_5$-$Arg_7$ preceeding the $Asn_{13}$ glycosylation site, has been suggested to provide the signal for GalNAc transferase. The introduction of a terminal GalNAc residue in the carbohydrate moiety enables a concomitant sulfation by a sulfotransferase. LH with carbohydrate moieties with terminal sulfate has a higher metabolic clearance rate than if sulfate is replaced by sialic acid. This is due to a hepatic reticuloendothelial cell receptor specific for the sulfated forms of LH. The bioactivity of the two forms at the receptor level is not distinguishable. It has been suggested that a rapid clearance rate of LH may be essential for generating the pulsatile variations seen in serum LH concentrations and may also influence the amplitude of the pulse seen in serum.

Recombinantly produced mammalian LH taking advantage of the mutated positions described above may find clinical use in areas of ovulation induction, treatment of conditions of secondary hypogonadism and of other fertility related disorders.

---

I claim:

1. An isolated DNA molecule consisting of the nucleotide sequence coding for a mammalian luteinizing hormone wherein the codon for the amino acid located at position 8 of the LHβ chain is replaced by a codon for arginine and the codon for isoleucine at position 15 of the LHβ chain is replaced by a codon for threonine.

2. The isolated DNA molecule consisting of the nucleotide sequence according to claim 1 wherein the amino acid replaced at position 8 is tryptophan.

3. The isolated DNA molecule consisting of the nucleotide sequence according to claim 1 or 2 wherein the luteinizing hormone is a human luteinizing hormone.

4. The isolated DNA molecule consisting of the nucleotide sequence according to claim 1 wherein the amino acid replaced at position 8 is leucine.

5. The isolated DNA molecule consisting of the nucleotide sequence according to claim 4 wherein the luteinizing hormone is a bovine, ovine or porcine luteinizing hormone.

6. The isolated DNA molecule consisting of the nucleotide sequence according to claim 1 wherein the codon for arginine at position 8 is CGG.

7. The isolated DNA molecule consisting of the nucleotide sequence according to claim 1 wherein the codon for threonine at position 15 is ACC.

* * * * *